United States Patent [19]
Gotti et al.

[11] Patent Number: 5,900,377
[45] Date of Patent: May 4, 1999

[54] METHOD FOR ISOLATING AND RADIOLABELING LEUKOCYTES FOR USE IN VIVO

[75] Inventors: Paul Richard Gotti; Trenton Todd Rees, both of Albuquerque, N.M.

[73] Assignee: Syncor International Corporation, Woodland Hills, Calif.

[21] Appl. No.: 08/810,234

[22] Filed: Mar. 3, 1997

[51] Int. Cl.$^6$ ................................ G01N 1/18; G01N 1/28
[52] U.S. Cl. ..................... 436/177; 210/787; 210/789; 436/57; 436/63; 436/174; 604/6
[58] Field of Search ................................. 436/63, 57, 174, 436/177; 604/4–6; 210/780, 781, 782, 767, 768, 787, 789

[56] References Cited

U.S. PATENT DOCUMENTS

| | | |
|---|---|---|
| 3,725,295 | 4/1973 | Eckelman et al. . |
| 4,311,688 | 1/1982 | Burchiel et al. . |
| 4,434,237 | 2/1984 | Dinarello . |
| 4,443,426 | 4/1984 | Thakur . |
| 4,452,774 | 6/1984 | Jones et al. . |
| 4,455,379 | 6/1984 | Bekesi et al. . |
| 4,456,690 | 6/1984 | Cais et al. . |
| 4,666,834 | 5/1987 | Bekesi et al. . |
| 5,093,104 | 3/1992 | Kaminsky . |
| 5,154,716 | 10/1992 | Bauman et al. ............................. 604/4 |
| 5,279,968 | 1/1994 | Hoogland et al. . |

OTHER PUBLICATIONS

Korbling et al., Biomedicine, (Jul. 1977), 26(4), pp. 275–283.

Zucker et al., Blood, (Nov. 1969), 34(5), pp. 591–600.

Martin et al., Experimental Hematology, (Feb. 1985), 13(2), pp. 79–86.

Kelbaek, European Journal of Nuclear Medicine, (Aug. 1986) 12(3), pp. 107–109.

Medline Abstract 84224014: McAfee et al., Seminars in Nuclear Medicine, (Apr. 1984), 14(2), pp. 83–106.

Merck Index, Tenth Edition, Entry No. 8307 (1983) Merck & Co., Inc.: Rahway N.J.

Cromwell, Leslie, Weibell, Fred J., and Pfeiffer, Erich A.; Biomedical Instrumentation and Measurements, Prentice–Hall, Inc., Englewood Cliffs, New Jersey, 1980, pp. 345–351.

Eisenstein, Edward and Schachman, H.K.; "Ultracentrifugation," Encylopedia of Human Biology, vol. 7, 199 1991, pp. 711–721.

Kelback, Henning and Jan Fogh, "Technetium–99m Labeling of Polymorphonuclear Leukocytes: Preparation with Two Different Stannous Agents," The Journal of Nuclear Medicine, vol. 26, No. 1, Jan. 1985, pp. 69–71.

Gutfilen, Bianca et al., "99mTC Labeling White Blood Cells With A Simple Technique:Clinical Application," Technical Notes, Annals of Nuclear Medicine, vol. 8, No. 1, 1994, pp. 85–89.

Indium In 111, Oxyquinoline Solution, Code In.15PA, Product Information Issued Jun., 1994: Medi–Physics, Inc., Amersham Healthcare, Arlington Heights, IL.

CIS–PYRO, Kit for the Preparation of Technetium TC 99m Pyrophasphate for Diagnostic Use, Manufactured in USA for CIS–US, Inc., Bedford, MA, Jan. 1995, 2P–001.

Ceretec, Kit for the Preparation of Technetium Tc99m Exametazime Injection, Product Information Issued Apr. 1995, Manufactured for Medi–Physics, Inc., Amersham Healthcare, Arlington Heights, IL.

*Primary Examiner*—Jan Ludlow
*Attorney, Agent, or Firm*—Pretty, Schroeder & Poplawski

[57] ABSTRACT

Disclosed is a method for separating leukocytes from platelets. Blood serum is added to a centrifuge tube. A suspension containing leukocytes and platelets is then added to form a layer on top of the blood serum, the layer having a density less than the density of the blood serum. The cells and the layers are centrifuged at a force and for a time sufficient to separate the leukocytes from the platelets. The resulting, isolated leukocytes are then recovered from the centrifuge tube. In some embodiments, a suspension of the leukocyte cells are pretreated by incubating with a stannous ion reducing agent, the suspension having a stannous ion concentration of from about 50 μg to about 1000 μg stannous ion per $10^8$ leukocyte cells. A suspension of the pretreated leukocyte cells is then incubated with a solution containing a technetium-99m (VII) salt, preferably sodium $^{99m}$Tc-pertechnetate, to radiolabel the leukocyte cells.

19 Claims, No Drawings

METHOD FOR ISOLATING AND RADIOLABELING LEUKOCYTES FOR USE IN VIVO

BACKGROUND OF THE INVENTION

1. Field of the Invention

This invention relates to the chemical arts. In particular, it relates to a method for isolating and radiolabeling leukocytes for subsequent in vivo use.

2. Description of the Related Art

A source of substantially pure leukocytes, i.e., leukocytes free from platelets, red blood cells and/or other components of whole blood, is important in a number of applications. One particularly significant application is to provide leukocytes for labeling with radioactive markers, such as technetium-99m and indium-111. The radiolabeled leukocytes are then used in a variety of diagnostic methods, including administration back into the human from whom the leukocytes were originally obtained. After the radiolabeled leukocytes have accumulated in the area to be imaged, they can be detected by scintigraphic techniques.

Several relatively simple methods, such as sedimentation and centrifugation, are known for separating leukocytes from red blood cells and/or other components of whole blood. Unfortunately, the leukocyte fraction obtained by such basic techniques contains platelets that can make the fraction unsuitable in certain applications, such as scintigraphy. Contamination of radiolabeled leukocytes by radiolabeled platelets, red blood cells and/or other components of whole blood is undesirable, because it exposes the patient to a higher than necessary dosage of the radioactive marker.

Accordingly, it is a desideratum for a method for isolating substantially pure leukocytes. Such a method must be relatively quick, simple and inexpensive, so that it can be easily employed by hospital and laboratory technologists.

Further, it is a desideratum for a method that produces substantially pure leukocytes without damaging the viability of the cells or leaving trace residues of reagents or other byproducts that would prevent the cells from being administered into a patient. For example, it is known that the effectiveness of centrifugation can be enhanced by using a discontinuous density gradient. With discontinuous density gradient centrifugation, an aqueous suspension of blood cells is layered over or underlayered a concentrated aqueous solution containing a nonreactive solute, such as a Ficoll-Hypaque mixture. The cells and gradients are then centrifuged at a rate sufficient to cause the cells to settle faster than they would under normal gravity. The spinning continues until the leukocytes collect at the gradient boundary. It is a disadvantage of discontinuous density centrifugation, however, that the nonreactive solutes, such as the Ficoll-Hypaque mixture, are not approved for use in humans. Therefore, the leukocytes isolated by this method cannot be used in vivo.

Once the substantially pure leukocytes have been isolated, there remains a further need for a simple and reproducible procedure for labeling the leukocytes with an effective and safe amount of a radioactive marker. If too little marker is incorporated, it may be impossible to detect the radiolabeled leukocytes once they have been reintroduced back into the patient. However, if too much marker is incorporated, the patient may be exposed to a higher than necessary dosage of the radioactive marker. Therefore, it is a further desideratum for an effective method for labeling substantially pure leukocytes with a suitable amount of a radioactive marker.

Accordingly, there has existed a definite need for a relatively quick, simple, and inexpensive method to isolate substantially pure leukocytes. There has existed a further need for a method to isolate substantially pure leukocytes for in vivo use. There has existed a still further need for a method to label the substantially pure leukocytes with an effective and safe amount of a radioactive marker. The present invention satisfies these and other needs and provides further related advantages.

SUMMARY OF THE INVENTION

Now in accordance with the invention, there has been discovered a method for separating leukocytes from a suspension also containing platelets. The leukocytes are separated by discontinuous density gradient centrifugation using blood serum as the densest layer.

First, blood serum is added to a centrifuge tube. Next, a suspension containing both leukocytes and platelets is carefully added to the centrifuge tube to form a layer distinct from the blood serum, the layer having a density less than the density of the blood serum. In some embodiments, multiple samples of blood are withdrawn from a human subject. The blood serum is obtained from one sample of blood and the suspension of leukocytes as platelets obtained from another. In preferred embodiments, the ratio of the volume of the serum to the volume of the leukocyte suspension is from about 10:1 to about 1:10.

The cells and the layers are then centrifuged at a force and for a time sufficient to separate the leukocytes from the platelets. In preferred embodiments, the tube is centrifuged at a force of from about 10 to about 300 G, more preferably about 100 G, and for a time of from about 2 to about 30 minutes, more preferably about 5 minutes. The resulting, isolated leukocyte cells are then recovered from the centrifuge tube.

The substantially pure leukocyte cells isolated by this method are especially suited for radiolabeling and subsequent administration to the human subject for leukocyte specific scintigraphy. In preferred embodiments, the substantially pure leukocyte cells are radiolabeled with a technetium-99m (IV) marker. In most preferred embodiments, a suspension of the leukocyte cells are pretreated by incubating with a stannous ion reducing agent, such as stannous chloride or a combination of stannous chloride and sodium pyrophosphate. The concentration of the stannous ion being from about 50 µg to about 1000 µg stannous ion per $10^8$ leukocyte cells. A suspension of the pretreated leukocyte cells are then incubated with a solution containing a technetium-99m (VII) salt, preferably sodium $^{99m}$Tc-pertechnetate, to reduce the technetium-99m (VII) salt and label the leukocyte cells.

DETAILED DESCRIPTION OF THE PREFERRED EMBODIMENTS

As required, details of preferred embodiments of the invention are disclosed. However, it is to be understood that the invention is not limited in its application to the details of the accompanying description, since the invention is capable of other embodiments and of being carried out in various ways. For example, the following description may concentrate on isolating leukocytes from a patient's peripheral blood for subsequent radiolabeling and administration to the patient. It should be readily apparent to the skilled artisan that the description with little or no modification might apply to obtaining the leukocytes to be isolated from other sources and for subsequently using the purified leukocytes for other purposes. Also, it is to be understood that the phraseology or terminology employed herein is for description and not of limitation.

At least two samples of peripheral blood are withdrawn from a patient, preferably using a single blood collection set, such as an evacuated tube blood collection set that includes a multiple sample leur adapter. With the leur adapter in place, at least one sample is collected into a centrifuge tube and coagulated. After coagulation, the contents are centrifuged, typically at a force of from about 100 to about 2000 G, for about 2 to about 20 minutes to produce an autologous blood serum supernatant.

The leur adapter is removed and replaced with a syringe to draw an additional sample from the patient. To prevent this sample from coagulating, the syringe contains an anticoagulant. Any anticoagulant, such as citrate or acidified citrate dextrose, may be used. The preferred anticoagulant is heparin in a final heparin concentration of 10 to 100 units/ml, preferably about 30 units/ml.

The uncoagulated sample is then separated into a red blood cell fraction and a plasma fraction containing leukocytes, platelets, residual red blood cells and other components of whole blood. The fractions are obtained by any conventional technique, such as centrifgation or sedimentation. In a presently preferred embodiment, sedimentation is used and the syringe inverted and clamped in a holder at an angle. The blood settles in this position for approximately one hour or until the two fractions are formed. The residual red blood cells settle to the bottom of the syringe, while leukocyte-rich plasma remains at the top. Hetastarch (available as Hespan (6% hetastarch in 0.9% NaCl) from DuPont, Wilmington, Del.), in a ratio of 1 ml hetastarch per 10 ml whole blood, can be used, if needed to facilitate the separation.

After the separation, the plasma fraction is transferred into a centrifuge tube and spun at a force of from about 100 to about 2000 G, for about 2 to about 30 minutes, to produce a supernatant and a pellet of leukocytes. The supernatant is then removed. The leukocytes, at this stage, contain a significant amount of platelets and are unsuitable or undesirable for a number of applications, including radiolabeling for leukocyte specific radiolabeling.

Now in accordance with the invention, the leukocytes are depleted of the platelets by discontinuous density centrifugation of a leukocyte suspension using blood serum to form the densest layer. If excessive, residual red blood cells are present in the leukocyte pellet resulting from the initial sedimentation and centrifugation (as determined by visual inspection), the pellet is suspended in a pharmaceutically acceptable aqueous liquid. Suitable liquids include isotonic (or nearly isotonic) solutions of salts, such as NaCl, or organic compounds, such as glucose. A 0.9% solution of NaCl is preferred. The suspension is then agitated in a clinical rotator for 10–15 minutes. The supernatant is discarded and the leukocyte pellet so obtained generally has a concentration of red blood cells less than about $10^5$/ml. if not, treatment in the clinical rotator is repeated until the desired red blood cell depletion is obtained. It is also possible to reduce the concentration of residual red blood cells to the desired level with an intermediate rocking step, as described in U.S. Pat. Nos. 5,093,104 and 5,279,968, which patents are herein incorporated by reference.

Using, as an example, a 15 ml centrifuge tube, 5 ml of the blood serum are added to the bottom of the centrifuge tube. In preferred embodiments, the blood serum will be autologous blood serum obtained as described above. It is also possible, however, to use blood serum obtained from alternative natural or synthetic sources.

An isotonic saline solution is added to the leukocyte pellet to form a suspension having a density less than the density of the blood serum. Five milliliters of the leukocyte suspension are carefully layered on top of the blood serum in the centrifuge tube without mixing the resulting two layers. The relative densities and amounts of the two layers are chosen so that the leukocytes will collect at the boundary between the upper layer of the suspension and the lower, high density layer. The relative densities and volumes of the two layers can vary depending upon the specific procedure, for example, in preferred embodiments, the ratio of the volume of serum to the volume of the suspension is from about 10:1 to about 1:10, most preferably about 1:1. The relative densities and volumes to be used in any particular procedure will be readily determinable by one skilled in the art for each procedure without undue experimentation.

The two layers are then centrifuged at a force and for a time sufficient to separate the leukocytes from the residual platelets. In presently preferred embodiments, the layers are centrifuged at a force from about 10 to about 300 G, more preferably about 100 G and for a time from about 2 minutes to about 30 minutes, more preferably about 5 minutes. The supernatant is then removed and leukocytes substantially depleted of platelets, as well as red blood cells and/or other components of whole blood recovered. Using the inventive method it is possible to isolate leukocyte factions having less than 96% of the platelets and less than 75% of the red blood cells, than were present in the original, whole-blood samples.

The leukocytes so obtained are especially useful for labeling with radioactive nuclides and subsequent use in leukocyte specific scintigraphy. The leukocytes can be labeled with any suitable radionuclide, including the radioactive isotopes of indium, technetium, ruthenium or gallium. Suitable radionuclide include indium-ill, indium-113m, indium-114m, indium-109, indium-110, technetium-99m, ruthenium-97, and gallium-67, with indium-111 and technetium-99m being preferred.

The source of the most preferred radionuclide starting material, $^{99m}$Tc-pertechnetate (technetium-99m (VII)), is preferably a water soluble salt, such as an alkaline or alkaline earth metal $^{99m}$Tc-pertechnetate salt. Sodium $^{99m}$Tc-pertechnetate, the preferred water soluble salt, can be obtained from a conventional $^{99}$Mo/$^{99m}$Tc generator.

In such preferred embodiments, the marker utilized to label the leukocytes is made by reducing the technetium-99m (VII) salt with a suitable reducing agent to form a reactive technetium-99m (IV) salt. Representative salts include the acetate, citrate and halide salts, such as the chloride, bromide, fluoride, and iodide salts. Preferred reducing agents include stannous ion reducing agents, such as stannous chloride alone or in combination with sodium pyrophosphate.

The formation of the reactive salt can be made to occur inside or outside of the cells to be radiolabeled. Accordingly, in some embodiments, a reactive technetium-99m (IV) salt is formed outside of the leukocyte cells. In preferred embodiments, the reactive salt is made using stannous chloride to reduce technetium-99m (VII), in the form of sodium $^{99m}$Tc-pertechnetate, to technetium-99m (IV). The resulting reactive technetium-99m (IV) salt is then mixed with a suitable carrier, such as pyrophosphate, oxyquinoline (oxine), or d, 1-hexamethyl proplyeneamine oxime (d,1-HMPAO), and the mixture used to incubate a suspension of leukocyte cells. In the next step, the leukocytes cells are labeled by simply combining the technetium-99m (IV)/carrier mixture with a suspension of leukocyte cells formed from an aqueous liquid, such as saline or blood plasma. After a sufficient period for incubation, the suspension is centrifuged and the radiolabeled leukocytes recovered.

In a presently most preferred embodiment, the leukocyte cells are pretreated with the stannous ion reducing agent, preferably in the form of a mixture of sodium pyrophosphate and stannous chloride and the reactive technetium-99m (IV) salt initially formed inside the leukocyte cell. The concentration of the stannous ion reducing agent is from about 50 $\mu$g to about 1000 $\mu$g, preferably from about 140 $\mu$g to about 1000 $\mu$g, of the stannous ion reducing per $10_8$ leukocyte cells. The thus pretreated leukocytes are then combined with a solution containing technetium-99m (VII), as sodium $^{99m}$Tc-pertechnetate, in a suitable carrier, and the mixture incubated, so that the radioactive marker is formed inside of the leukocyte cells. After incubation, the resulting technetium-99m radiolabeled leukocyte cells are recovered.

The resulting marker can have any suitable amount of radioactivity, with the understanding that too little activity may make subsequent detection difficult or impossible and too much radioactivity may subject the patient to undesirable levels of the radionuclide. Generally, the radioactivity of the marker will be at least 90% of the radioactivity of the salt of the radionuclide utilized as the starting material. It is generally preferred to form radioactive markers containing from about 0.1 mCi to about 50 mCi, with markers containing from about 0.5 mCi to about 30 mCi being especially preferred. Typically, these radioactive markers are formed in solutions containing radioactive concentrations of from about 0.05 mCi to 100 mCi, preferably from about 20 to about 50 mCi, per ml.

The following example is intended to further illustrate the invention and is not a limitation thereon.

EXAMPLE

Blood Collection

Whole blood was obtained from a human subject using a Vacuutainer blood collection set (19×¾12" tubing with multiple sample leur adapter). First, three 10 ml samples were collected in the three red top tubes. Then, the leur adapter was replaced with a 60 ml syringe containing 1000 units of Heparin and the syringe used to collect 60 ml of blood.

Preparation of Autologous Blood Serum

The three ten ml samples collected in the red top tubes were allowed to clot at room temperature. The blood was then centrifuged at 1000 G for 5 minutes and the resulting autologous serum supernatant recovered.

Preparation of Leukocytes

The 60 ml syringe was inverted and clamped at a 60° angle in a holder. The blood settled in this position for approximately 1 hour until it had separated into a plasma fraction and a red blood cell fraction. After sedimentation, an extension set was used to express the plasma fraction into a 50 ml centrifuge tube. The buffy coat layer was collected, but not the red blood cells.

The plasma fraction was centrifuged at 250 G for ten minutes to produce a supernatant and a pellet of leukocytes. After removing the supernatant, the pellet was resuspended in 6 ml of 0.9% NaCl and agitated in a clinical rotator for 10–15 minutes. The resulting supernatant was removed and the pellet resuspended in 5 ml of 0.9% NaCl.

Five ml of the autologous serum were placed in the bottom of a 15 ml centrifuge tube. Five ml of the leukocyte suspension were then carefully layered over the serum and the tube centrifuged at 100 G for 5 minutes. The supernatant was removed to produce a pellet of leukocytes substantially free of platelets.

Radiolabeling of the Leukocytes

The pellet of leukocytes was resuspended in 1–2 ml 0.9% NaCl. Ten ml of 0.9% NaCl was added to a vial of CIS-PYRO, obtained from CIS-US, Bedford, Mass. Each 10 ml vial contains 12.0 ml of sodium pyrophosphate, 2.8 mg minimum stannous tin as stannous chloride dehydrate and 4.9 mg maximum total tin as stannous chloride dehydrate. One-half ml of the resulting solution (140 $\mu$g–245 $\mu$g of Sn) was added to the leukocyte suspension and the mixture incubated at room temperature for 15 minutes with occasional swirling. The mixture was then centrifuged at 100 G for 5 minutes and the supernatant removed leaving a leukocyte pellet.

Excess tin was removed by adding 3 ml 0.9% NaCl to the pellet and gently swirling to resuspend the cells. The suspension was centrifuged at 100 G for 5 minutes and the supernatant removed.

The resulting leukocyte pellet was resuspended in 1–2ml 0.9 ml NaCl and 40–50 mCi $^{99m}$TcO$_4$ (0.5 ml), from a fresh elution, added. The suspension was incubated for 15 minutes, with swirling every 5 minutes. After incubation, the suspension was centrifuged at 100 G for 5 minutes and the supernatant removed to produce the radiolabeled leukocytes.

We claim:

1. A method for isolating leukocytes from a suspension containing leukocytes and platelets comprising:
   adding blood serum to a centrifuge tube;
   adding a suspension containing leukocytes and platelets to the centrifuge tube to form a layer distinct from the blood serum, the layer having a density less than the density of the blood serum;
   centrifuging the tube at a force and for a time sufficient to separate the leukocytes from the platelets; and
   recovering the isolated leukocytes from the centrifuge tube.

2. The method in accordance with claim 1 wherein the ratio of the volume of the serum to the volume of the leukocyte suspension is from about 10:1 to about 1:10.

3. The method in accordance with claim 1 wherein the tube is centrifuged at a force of from about 10 to about 300 G and for a time of from about 2 to about 30 minutes.

4. The method in accordance with claim 1 wherein the leukocyte suspension is added to form a layer on top of the blood serum.

5. A method for isolating leukocytes from whole blood comprising:
   adding blood serum to a centrifuge tube;
   separating whole blood into a red blood cell fraction and a leukocyte fraction containing platelets;
   forming a suspension containing the leukocytes and the platelets;
   adding the suspension to the centrifuge to form a layer distinct from the blood serum, the layer having a density less than the density of the blood seru
   centrifuging the tube at a force and for a time sufficient to separate the leukocytes from the platelets; and
   recovering the isolated leukocytes from the centrifuge tube.

6. The method in accordance with claim 5 wherein the whole blood is separated by centrifugation or sedimentation.

7. The method in accordance with claim 5 wherein the whole blood is separated by sedimentation.

8. The method in accordance with claim 5 wherein the ratio of the volume of the serum to the volume of the leukocyte suspension is from about 10:1 to about 1:10.

9. The method in accordance with claim 5 wherein the concentration of residual red blood cells in the suspension is less than about $10^5$ cells per ml.

10. The method in accordance with claim 5 wherein the tube is centrifuged at a force of from about 10 to about 300 G and for a time of from about 2 to about 30 minutes.

11. The method in accordance with claim 5 wherein the leukocyte suspension is added to form a layer on top of the blood serum.

12. A method for isolating leukocytes for use in vivo in a human subject comprising:

withdrawing first and second samples of blood from a human subject;

preparing blood serum from the first sample of blood;

adding the blood serum to a centrifuge tube;

separating the second blood sample into a red blood cell fraction and a fraction containing leukocytes and platelets;

forming a suspension containing the leukocytes and platelets;

adding the suspension to the centrifuge to form a layer distinct from the blood serum, the layer having a density less than the density of the blood serum;

centrifuging the tube at a force and for a time sufficient to separate the leukocytes from the residual platelets; and recovering the isolated leukocytes from the centrifuge tube.

13. The method in accordance with claim 12 wherein the whole blood is separated by centrifugation or sedimentation.

14. The method in accordance with claim 12 wherein the whole blood is separated by sedimentation.

15. The method in accordance with claim 12 wherein the ratio of the volume of the serum to the volume of the leukocyte suspension is from about 10:1 to about 1:10.

16. The method in accordance with claim 12 wherein the concentration of residual red blood cells in the suspension is less than about $10^5$ cells per ml.

17. The method in accordance with claim 12 wherein the tube is centrifuged at a force of from about 10 to about 300 G and for a time of from about 2 to about 30 minutes.

18. The method in accordance with claim 12 further comprising labeling the isolated leukocytes with a radionuclide.

19. The method in accordance with claim 18 wherein the radionuclide is technetium-99m or indium-111.

* * * * *